United States Patent
Wang et al.

(10) Patent No.: US 11,365,434 B2
(45) Date of Patent: Jun. 21, 2022

(54) ENZYMATIC METHOD FOR PRODUCING FATTY ACID BORNYL ESTER

(71) Applicant: Jiangnan University, Wuxi (CN)

(72) Inventors: Xiaosan Wang, Wuxi (CN); Yu Zhao, Wuxi (CN); Liang Gao, Wuxi (CN); Qingzhe Jin, Wuxi (CN); Xingguo Wang, Wuxi (CN)

(73) Assignee: Jiangnan University, Wuxi (CN)

( * ) Notice: Subject to any disclaimer, the term of this patent is extended or adjusted under 35 U.S.C. 154(b) by 28 days.

(21) Appl. No.: 17/024,713

(22) Filed: Sep. 18, 2020

(65) Prior Publication Data

US 2021/0130859 A1 May 6, 2021

(30) Foreign Application Priority Data

Nov. 5, 2019 (CN) .......................... 201911069862.9

(51) Int. Cl.
*C12N 9/20* (2006.01)
*C12P 7/6454* (2022.01)
*C12P 7/6472* (2022.01)

(52) U.S. Cl.
CPC ........... *C12P 7/6454* (2013.01); *C12P 7/6472* (2013.01); *C12Y 301/01003* (2013.01)

(58) Field of Classification Search
CPC ..................... C12P 7/6454; C12Y 301/01003
USPC ........................................................ 435/198
See application file for complete search history.

(56) References Cited

PUBLICATIONS

Sonomoto & Tanaka, Ann. N.Y. Acad. Sci.; (1988) 542, 235-239 (Year: 1988).*

* cited by examiner

*Primary Examiner* — Tekchand Saidha
(74) *Attorney, Agent, or Firm* — Idea Intellectual Limited; Margaret A. Burke; Sam T. Yip

(57) ABSTRACT

The present invention provides an enzymatic method for producing a fatty acid bornyl ester including using borneol and a fatty acid as a substrate for reaction and adding a lipase in a solvent system or a solvent-free system to catalyze the esterification reaction for a period of time to obtain fatty acid bornyl ester. The present method preferably uses fatty acids or their derivatives as acyl donors to prepare fatty acid bornyl esters. By utilizing the characteristics of the substrate, the synthesis process is simple; the reaction efficiency is high; and the content of fatty acid bornyl ester is up to 97%.

11 Claims, 2 Drawing Sheets

ENZYMATIC METHOD FOR PRODUCING FATTY ACID BORNYL ESTER

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

CROSS-REFERENCES TO RELATED APPLICATIONS

This application claims priority to Chinese patent application No. 2019110698629 filed on Nov. 5, 2019, and the disclosure of which is incorporated herein by reference in its entirety.

FIELD OF THE INVENTION

The present invention belongs to the preparation of compounds such as fatty acid bornyl ester in the field of organic chemistry. More specifically, the present invention relates to an enzymatic method for producing a fatty acid bornyl ester.

BACKGROUND OF THE INVENTION

Borneol is widely used in industries such as pharmaceutical and medicine, perfume, cosmetic, food, etc. For pharmaceutical and medicine field, borneol is not only a good penetration enhancer, but also with the functions of nerve protection, regulation of the central nervous system in both directions, anti-inflammation and analgesic, and anti-pathogenic microorganisms and anti-cancer. However, there are some defects occurred in the actual use of borneol: first, the pharmacological effect of borneol is limited mainly due to its poor stability and limited water and fat solubility; second, borneol has certain toxic side effects; third, the strong flavor of borneol will cover the flavor of other substances. In comparison with borneol, its derivatives not only can retain the original effects of the borneol but also can reduce toxicity, which are stable and easy to store, as well as having other functions. According to relevant reports, conjugated bornyl linoleate has obvious antitumor effects; bornyl methoxybenzoate possess good antimicrobial ability; and bornyl salicylate has high anti-inflammatory effects, etc.

Fatty acid bornyl ester is one of borneol derivatives. The major methods for synthesizing fatty acid bornyl ester are chemical methods. Chemical methods usually use one kind of strong acid as a catalyst, or conduct Steglich esterification, etc. The reaction requires a higher temperature and organic solvents, etc. High-temperature reaction usually causes various product quality problems such as color and odor, and have a high requirement for the equipment used, whereas using organic solvents is likely to cause environment pollution. For example, the Chinese patent application number CN201711203302.9 discloses a fatty acid borneol ester, which is made by condensing borneol with fatty acid in the presence of a condensing agent. During the reaction, the conditions are mild and the cost is low, but the reaction is incomplete and easy to produce by-products. Meanwhile, residual solvents may have certain impact on the safety of the product. Compared with the non-enzymatic chemical methods, the enzymatic method has mild reaction conditions and catalytic specificity, and ultimately no by-products are generated.

At present, there are few reports of enzymatic preparation of fatty acid bornyl esters, and it is difficult to synthesize fatty acid bornyl esters since borneol is a secondary alcohol with large steric hindrance. Therefore, there is a need in the art for a method for preparing fatty acid bornyl esters by an enzymatic process, which overcomes the problems of poor safety and low production efficiency encountered in the art while achieving mild reaction conditions, and no by-products are generated therein.

SUMMARY OF THE INVENTION

This section aims to summarize some aspects of the embodiments of the present invention and to briefly describe some preferred embodiments. Simplification or omission may be made in this section, the abstract of the specification, and the title to avoid obscuring the purposes of this section, the abstract of the specification, and the title. Such simplification or omission may not be used to limit the scope of the present invention.

The present invention is provided in view of above and/or the existing problems faced in the preparation of fatty acid bornyl ester.

Therefore, as one object of the present invention, there is provided a method for producing a fatty acid bornyl ester by an enzymatic process to overcome the technical hurdles in the conventional method for preparing a fatty acid bornyl ester.

In view of the technical problems as above-mentioned, there is provided an enzymatic method for producing a fatty acid bornyl ester including using a borneol and a fatty acid as a substrate for reaction and adding a lipase in a solvent system or a solvent-free system to catalyze an esterification reaction for a period of time to obtain the fatty acid bornyl ester.

In one embodiment, the lipase is derived from *Candida rugosa*.

In another embodiment, the lipase is selected from one or more of Lipase AYS or Lipase AY30.

In yet another embodiment, the fatty acyl donor is selected from one or more of free fatty acids and their derivatives.

In other embodiment, the fatty acid derivatives are selected from one or more of fatty acid methyl ester, fatty acid ethyl ester and glyceride.

In anther embodiment, a molar ratio of the borneol to the fatty acyl donor is 1:1-6.

In yet another embodiment, the esterification reaction has a reaction temperature of 20-80° C.

In other embodiment, the amount of lipase accounts for 2-30% of total mass of the borneol and fatty acyl donor.

In anther embodiment, the esterification reaction has a reaction time ranging from 10 to 100 hours.

In yet another embodiment, a solvent used in the solvent system is selected from one or more of n-hexane, isohexane and petroleum ether.

The present invention has the following advantages:

(1) The present invention provides a method for producing a fatty acid bornyl ester by an enzymatic process, which preferably uses fatty acids or their derivatives as acyl donors to prepare fatty acid bornyl esters. By utilizing the characteristics of the substrate, the synthesis process is simple, the reaction efficiency is high, and the content of fatty acid bornyl ester is up to 97%.

(2) Compared with chemical methods, the present enzymatic preparation method has several advantages such as milder reaction conditions, better selectivity, higher catalytic efficiency, easily removable catalysts, fewer by-products, and better product quality.

(3) The present method for producing a fatty acid bornyl ester by an enzymatic process has high practicability, which is good for promoting large-scale industrialization and having a broad application potential.

DETAILED DESCRIPTION

Figure 1:
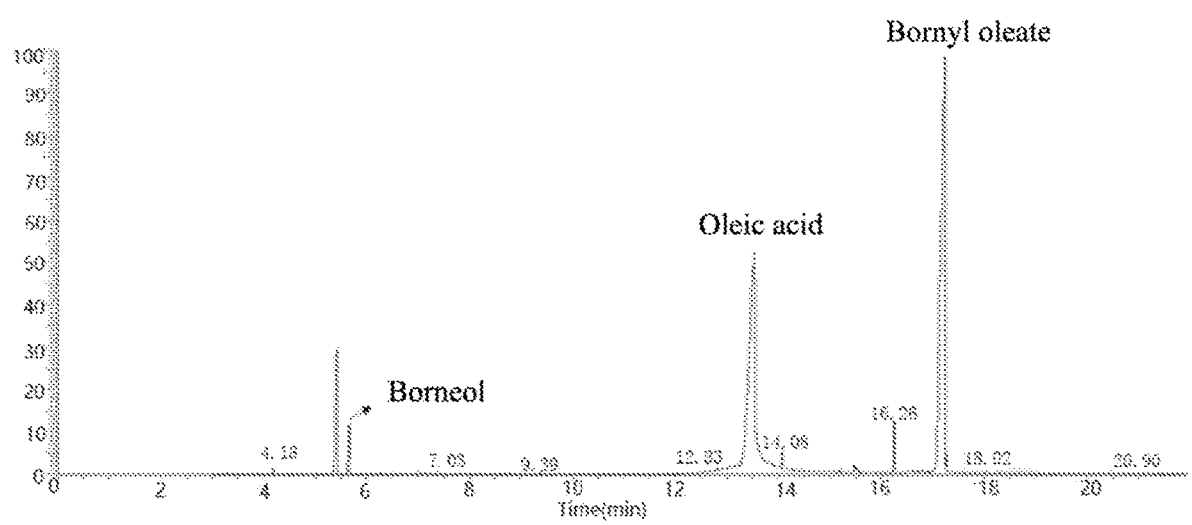
FIG. 1 depicts a GC chromatogram (gas chromatogram) of bornyl oleate produced through the esterification reaction between borneol and oleate in Example 5.
Figure 2:
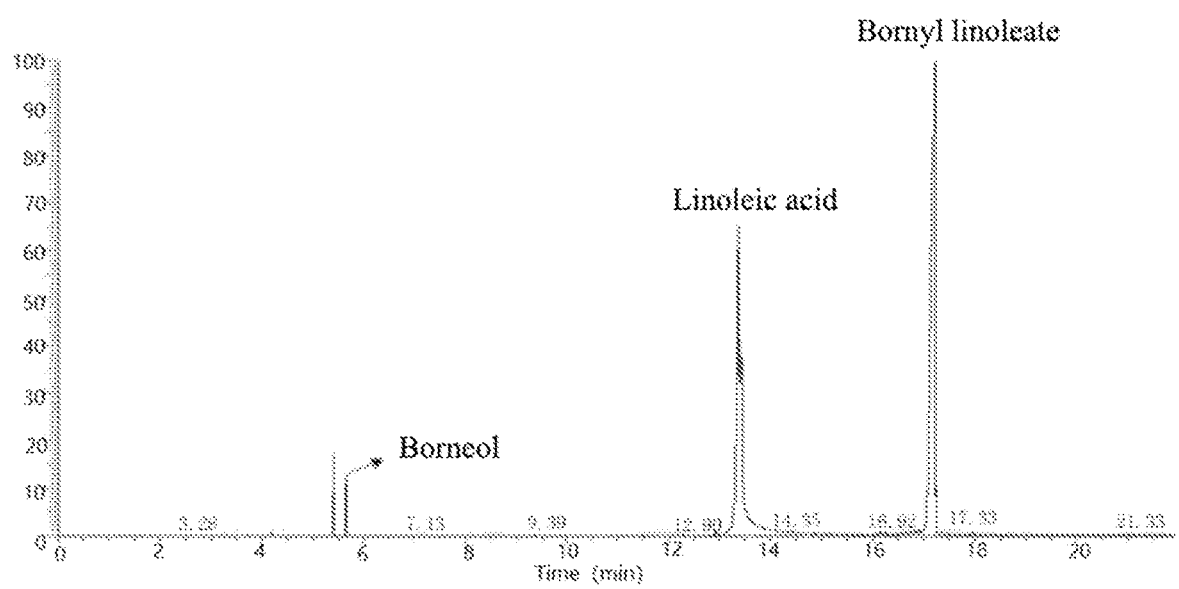
FIG. 2 depicts a GC chromatogram (gas chromatogram) of bornyl linoleate produced through the esterification reaction between borneol and oleate in Example 9.

In the present disclosure, both Lipase AYS and Lipase AY30 are derived from *Candida rugosa*, where lipase AYS was purchased from Sigma (Item No.: L1754), and lipase AY30 was purchased from Amano Enzyme CO., LTD.

Borneol (75%) used in the present invention comes from Land of Nature Biotechnology CO., LTD; oleic acid (85%) comes from ALADDING CO., LTD; linoleic acid (94%) was made by inventor's own laboratory; methyl oleate (85%) comes from ALADDING CO., LTD; and ethyl oleate (75%) comes from ALADDING CO., LTD.

EXAMPLE

Example 1

(1) Batch enzyme reaction was carried out in a batch-type stirring tank reactor. Under a solvent-free system, 2 mmol of borneol and 8 mmol of oleic acid were mixed, and Lipase AYS, which accounts for 8% of the total mass of borneol and oleic acid, was added and acted as a catalyst. The mixture was stirred at 30° C. for 48 hours under normal pressure.

(2) After completion of the reaction, the lipase was removed through a centrifugal sedimentation method, and the resulting product was analyzed by GC chromatography. The results showed that bornyl oleate had a conversion rate of 71.34%.

Example 2

(1) Batch enzyme reaction was carried out in a batch-type stirring tank reactor. Under a solvent-free system, 2 mmol of borneol and 6 mmol of oleic acid were mixed, and Lipase AY30, which accounts for 10% of the total mass of borneol and oleic acid, was added and acted as a catalyst. The mixture was stirred at 50° C. for 48 hours under normal pressure.

(2) After completion of the reaction, the lipase was removed through a centrifugal sedimentation method, and the resulting product was analyzed by GC chromatography. The results showed that bornyl oleate had a conversion rate of 42.25%.

Example 3

(1) Batch enzyme reaction was carried out in a batch-type stirring tank reactor. Under a solvent system with 4 ml n-hexane, 2 mmol of borneol and 4 mmol of lauric acid were mixed, and Lipase AYS, which accounts for 10% of the total mass of borneol and lauric acid, was added and acted as a catalyst. The mixture was stirred at 45° C. for 48 hours under normal pressure.

(2) After completion of the reaction, the lipase was removed through a centrifugal sedimentation method, and the resulting product was analyzed by GC chromatography. The results showed that bornyl oleate had a conversion rate of 24.06%.

Example 4

(1) Batch enzyme reaction was carried out in a batch-type stirring tank reactor. Under a solvent-free system, 2 mmol of borneol and 2 mmol of oleic acid were mixed, and Lipase AYS, which accounts for 8% of the total mass of borneol and oleic acid, was added and acted as a catalyst. The mixture was stirred at 60° C. for 24 hours under normal pressure.

(2) After completion of the reaction, the lipase was removed through a centrifugal sedimentation method, and the resulting product was analyzed by GC chromatography. The results showed that bornyl oleate had a conversion rate of 63.61%.

Example 5

(1) Batch enzyme reaction was carried out in a batch-type stirring tank reactor. Under a solvent-free system, 2 mmol of borneol and 6 mmol of oleic acid were mixed, and Lipase AYS, which accounts for 8% of the total mass of borneol and oleic acid, was added and acted as a catalyst. The mixture was stirred at 45° C. for 48 hours under normal pressure.

(2) After completion of the reaction, the lipase was removed through a centrifugal sedimentation method, and the resulting product was analyzed by GC chromatography. The results showed that bornyl oleate had a conversion rate of 95.62%.

Example 6

(1) Batch enzyme reaction was carried out in a batch-type stirring tank reactor. Under a solvent-free system, 2 mmol of borneol and 5 mmol of oleic acid were mixed, and Lipase AYS, which accounts for 8% of the total mass of borneol and oleic acid, was added and acted as a catalyst. The mixture was stirred at 45° C. for 80 hours under normal pressure.

(2) After completion of the reaction, the lipase was removed through a centrifugal sedimentation method, and the resulting product was analyzed by GC chromatography. The results showed that bornyl oleate had a conversion rate of 96.95%.

Example 7

(1) Batch enzyme reaction was carried out in a batch-type stirring tank reactor. Under a solvent system with 3 ml petroleum ether, 2 mmol of borneol and 4 mmol of oleic acid were mixed, and Lipase AYS, which accounts for 8% of the total mass of borneol and oleic acid, was added and acted as a catalyst. The mixture was stirred at 45° C. for 40 hours under normal pressure.

(2) After completion of the reaction, the lipase was removed through a centrifugal sedimentation method, and the resulting product was analyzed by GC chromatography. The results showed that bornyl oleate had a conversion rate of 57.28%.

Example 8

(1) Batch enzyme reaction was carried out in a batch-type stirring tank reactor. Under a solvent-free system, 2 mmol of borneol and 4 mmol of methyl oleate were mixed, and Lipase AYS, which accounts for 8% of the total mass of borneol and methyl oleate, was added and acted as a catalyst. The mixture was stirred at 45° C. for 48 hours under normal pressure.

(2) After completion of the reaction, the lipase was removed through a centrifugal sedimentation method, and the resulting product was analyzed by GC chromatography. The results showed that bornyl oleate had a conversion rate of 14.48%.

Example 9

(1) Batch enzyme reaction was carried out in a batch-type stirring tank reactor. Under a solvent-free system, 2 mmol of borneol and 4 mmol of linoleic acid were mixed, and Lipase AYS, which accounts for 8% of the total mass of borneol and linoleic acid, was added and acted as a catalyst. The mixture was stirred at 45° C. for 48 hours under normal pressure.

(2) After completion of the reaction, the lipase was removed through a centrifugal sedimentation method, and the resulting product was analyzed by GC chromatography. The results showed that bornyl oleate had a conversion rate of 94.04%.

Example 10

(1) Batch enzyme reaction was carried out in a batch-type stirred tank reactor. Under a solvent-free system, 2 mmol of borneol and 4 mmol of linoleic acid were mixed, and Lipase AYS, which accounts for 18% of the total mass of borneol and linoleic acid, was added and acted as a catalyst. The mixture was stirred at 45° C. for 48 hours under normal pressure.

(2) After completion of the reaction, the lipase was removed through a centrifugal sedimentation method, and the resulting product was analyzed by GC chromatography. The results showed that bornyl oleate had a conversion rate of 97.58%.

Example 11

(1) Batch enzyme reaction was carried out in a batch-type stirring tank reactor. Under a solvent-free system, 2 mmol of borneol and 4 mmol of linoleic acid were mixed, and Lipase AYS, which accounts for 4% of the total mass of borneol and linoleic acid, was added and acted as a catalyst. The mixture was stirred at 45° C. for 48 hours under normal pressure.

(2) After completion of the reaction, the lipase was removed through a centrifugal sedimentation method, and the resulting product was analyzed by GC chromatography. The results showed that bornyl oleate had a conversion rate of 89.21%.

Example 12

(1) Batch enzyme reaction was carried out in a batch-type stirring tank reactor. Under a solvent-free system, 2 mmol of borneol and 6 mmol of linoleic acid were mixed, and Lipase AYS, which accounts for 8% of total mass of borneol and linoleic acid, was added and acted as a catalyst. The mixture was stirred at 45° C. for 10 hours under normal pressure.

(2) After completion of the reaction, the lipase was removed through a centrifugal sedimentation method, and the resulting product was analyzed by GC chromatography. The results showed that bornyl oleate had a conversion rate of 91.62%.

Example 13

Based on Example 5, different enzymes (e.g. Lipozyme 435, NS40086 and Lipase AY30) were used for treatment while keeping other conditions to investigate the effect of different enzyme treatment on the conversion rate of bornyl oleate. The experimental design and results were shown in Table 1.

TABLE 1

|  | Trial 1 | Trial 2 | Trial 3 |
|---|---|---|---|
| Enzyme | Lipase lipozyme 435 | Specific lipase NS40086 | Lipase AY30 |
| Conversion rate of bornyl oleate (%) | 2.37% | 2.40% | 40.12% |

It could be seen that an immobilized enzyme such as lipase Lipozyme 435 derived from *Candida Antarctica* B, and sn-1,3-specific lipase NS40086 derived from *Rhizomucor miehei* was used. The result showed that the esterification rates were 2.37% and 2.40% respectively. In addition, free lipases AYS and AY30 derived from *Candida rugosa* were used. The result showed that the esterification rates were 95.62% and 40.12% respectively. It could be seen that all the lipases Lipozyme 435, NS40086 and AY30 had catalytic activity, but their catalytic efficiency was not as good as enzyme AYS. Lipase NS40086 is sn-1,3-specific, which makes it unable to exhibit a good catalytic activity during the catalytic reaction of bornyl oleate; Lipozyme 435 has no specificity, but its catalytic efficiency was still low, which may be because the lipase-catalyzed reaction of bornyl oleate was based on a substrate specific enzymatic reaction, and therefore different substrates may affect the catalytic activity of the lipase; Lipase AY30 and Lipase AYS belonged to the same CRL family, but Lipase AYS had strong catalytic activity for secondary alcohol and had non-acyl selectivity compared to Lipase AY30. Therefore, the catalytic efficiency of Lipase AYS was significantly higher than other lipases.

Based on Example 6, the effects of different enzyme contents, reaction temperature and time on the conversion rate of bornyl oleate were studied. The experimental design and results were shown in Table 2, Table 3 and Table 4, respectively.

TABLE 2

|  | Trial 4 | Trial 6 | Trial 7 | Trial 8 |
|---|---|---|---|---|
| Content of enzyme (%) | 6 | 8 | 10 | 12 |
| Conversion rate of bornyl oleate (%) | 90.68 | 95.62 | 95.30 | 95.17 |

It could be seen that when the amount of enzyme was less than 8%, adding the enzyme could increase the chance of contact between the enzyme and the substrate, thereby accelerating the esterification rate, and the content of bornyl oleate produced per unit time was continuously increasing; when the amount of enzyme was greater than 8%, the esterification rate tended to be stable or even lower. This is because Lipase AYS is a free enzyme that has not been immobilized and is in a powdered form. When excess of Lipase AYS is added, the viscosity and mass transfer resistance of the system will increase. If the contact between the active site of the lipase and the substrate had reached a saturation level, the excess lipase could not fully participate in the reaction.

TABLE 3

|  | Trial 9 | Trial 10 | Trial 11 | Trial 12 |
|---|---|---|---|---|
| Reaction temperature (° C.) | 35 | 40 | 45 | 50 |
| Conversion rate of bornyl oleate (%) | 82.26 | 88.13 | 95.62 | 94.33 |

Referring to Table 3, increasing the reaction temperature could improve the compatibility of the substrate, strengthen the interaction between the substrates, and increase the activity of lipase, thereby increasing the reaction rate. However, an excessively high reaction temperature might destroy the active site of the enzyme and continuously reduce the catalytic activity.

TABLE 4

|  | Trial 13 | Trial 14 | Trial 15 | Trial 16 |
|---|---|---|---|---|
| Reaction time (hour) | 10 | 24 | 48 | 72 |
| Conversion rate of bornyl oleate (%) | 71.48 | 92.30 | 95.62 | 95.95 |

Referring to Table 4, the esterification reaction continuously performed as time increases. When the reaction time exceeded 72 hours, on the one hand the esterification reaction was reversible, which meant that the esterification reaction products has a risk of being hydrolyzed again; on the other hand the oleic acid in the substrate had a risk of being oxidized as time goes by, which was not conducive to the continuation of the reaction.

In summary, the optimal amount of enzyme was 8%, the reaction time was 48 hours, and the reaction temperature was 45° C. Under these conditions, the bornyl oleate had a conversion rate of 95.62%.

Example 14

Based on Example 5, the effects of different fatty acyl donors and their contents thereof on the conversion rate of bornyl oleate were studied. The experimental design and results were shown in Table 5.

TABLE 5

|  | Trial 17 | Trial 18 |
|---|---|---|
| Fatty acyl donors | Methyl oleate | Ethyl oleate |
| Molar ratio of bo | 1:2 | 1:2 |
| Conversion rate of bornyl oleate (%) | 14.48% | 9.24% |

Referring to Table 5, when using methyl oleate or ethyl oleate as an acyl donor for transesterification, bornyl oleate had a very low conversion rate because new ester formed during the process was not as stable as the reactant such as methyl oleate or ethyl oleate, or the new ester was not continuously distilled out during the process, resulting in a low conversion rate of bornyl oleate.

In the prior art, borneol was a secondary alcohol with large steric hindrance. There were some challenges to synthesizing fatty acid bornyl ester. In the present disclosure, Lipase AYS was used as a catalyst, which had a strong catalytic activity for secondary alcohol reaction and a non-acyl selectivity. The catalytic mechanism of Lipase AYS was to catalyze a triad and amino acid residues of oxyanion pores. In a substrate binding site, changing Ala and Ser450 may prevent direct spatial conflicts. The substrate binding site of Lipase AYS was located in a long and extremely hydrophobic internal channel, and once the compound entered the channel, catalysis was carried out in two consecutive steps. In an acylation phase, a hydroxyl group that responsible for catalyzing Ser triggered a nucleophilic attack on a carbonyl group of the substrate, forming a first negatively charged tetrahedral intermediate, which was stabilized by the specific residues of the oxyanion pore. Then, the alcohol portion of the substrate accepted protons and was released, while the acid portion formed a covalent acylase intermediate, which was finally destroyed by water, alcohol, acid or ester molecule. In the choice of reaction conditions, the hydrophobic environment, temperature, substrate ratio, amount of enzyme added and reaction time that suitable for the enzyme were selected to maximize the enzyme activity.

Borneol is a secondary alcohol with large steric hindrance. For this reason, the disclosure used Lipase AYS, which could catalyze the regional and stereoselective transesterification reaction, as a catalyst. At present, most preparation methods of borneol derivatives adopt chemical methods, that is, using chemical catalysts to catalyze the reaction. For example, some scholars had found that when synthesizing bornyl methoxybenzoate compounds, p-toluenesulfonic acid could be used as a catalyst, and toluene acted as a solvent; other scholars had found that when synthesizing bornyl nicotinate, DMAP could be used as a catalyst, DCC acted as a dehydrating agent, and dichloromethane acted as a solvent. The esterification rate reached 80%; another scholars had found that when synthesizing fatty acid bornyl ester, it could also be synthesized through Steglich esterification (DIC/DMAP method), and the yield was in a range of 20-85%. From the existing technology for synthesizing borneol derivatives, catalytic methods inevitably use chemical catalysts that are toxic to the environment and the human body, and the reaction conditions are often accompanied by solvents and high temperatures, which not only affect the equipment and the environment, but also make the products prone to residues of solvents and catalysts, and are not suitable for applying in food, medicine or other fields that require high safety.

In contrast, the present invention adopts the following solutions: the present invention uses enzymes which are friendly to the environment and the human body as catalysts. In addition, when a long-chain unsaturated fatty acid is used as a substrate, the fatty acid has a very good compatibility with the substrate without any organic solvent. The reaction conditions are mild, and the esterification rate is up to 97%, the yield is high and the safety of the resulting product has been guaranteed. It is particularly suitable to apply in food, medicine and other fields that require higher safety.

The present invention provides a method for producing a fatty acid bornyl ester by an enzymatic process, which utilize characteristics of the substrate to reach simple synthesis process, high reaction efficiency, and the content of fatty acid bornyl ester is up to 97%; the present invention utilizes a lipase with a specificity and high efficiency to carry out esterification reaction and obtain fatty acid bornyl esters. After further optimization, the reaction conditions are optimized so that the method for preparing fatty acid bornyl ester has several advantages such as milder conditions, excellent selectivity, higher catalytic efficiency, easily removable catalysts, fewer by-products, and good product quality. It can be seen that the present method for producing a fatty acid bornyl ester by an enzymatic process has a strong practicability, which is good for promoting large-scale industrialization and having a broad application prospect.

What is claimed is:

1. An enzymatic method for producing a fatty acid bornyl ester comprising using a borneol and a fatty acid as a substrate for reaction and adding a lipase in a solvent system or a solvent-free system to catalyze an esterification reaction for a period of time to obtain the fatty acid bornyl ester, wherein the lipase is obtained from *Candida rugosa*.

2. The enzymatic method for producing a fatty acid bornyl ester of claim 1, wherein the lipase is selected from one or more of Lipase AYS or Lipase AY30.

3. The enzymatic method for producing a fatty acid bornyl ester of claim 1, wherein the fatty acyl donor is selected from one or more of free fatty acids and their derivatives.

4. The enzymatic method for producing a fatty acid bornyl ester of claim 2, wherein the fatty acid derivatives are selected from one or more of fatty acid methyl ester, fatty acid ethyl ester and glyceride.

5. The enzymatic method for producing a fatty acid bornyl ester of claim 1, wherein a molar ratio of the borneol to the fatty acyl donor is 1: 1-6.

6. The enzymatic method for producing a fatty acid bornyl ester of claim 3, wherein a molar ratio of the borneol to the fatty acyl donor is 1: 1-6.

7. The enzymatic method for producing a fatty acid bornyl ester of claim 1, wherein the esterification reaction has a reaction temperature of 20-80° C.

8. The enzymatic method for producing a fatty acid bornyl ester of claim 1, wherein the amount of lipase accounts for 2-30% of total mass of the borneol and fatty acyl donor.

9. The enzymatic method for producing a fatty acid bornyl ester of claim 7, wherein the amount of lipase accounts for 2-30% of total mass of the borneol and fatty acyl donor.

10. The enzymatic method for producing a fatty acid bornyl ester of claim 1, wherein the esterification reaction has a reaction time ranging from 10 to 100 hours.

11. The enzymatic method for producing a fatty acid bornyl ester of claim 1, wherein a solvent used in the solvent system is selected from one or more of n-hexane, isohexane and petroleum ether.

* * * * *